United States Patent [19]

Clark et al.

[11] Patent Number: 4,968,707
[45] Date of Patent: Nov. 6, 1990

[54] OXAZOLIDIN-2-ONE DERIVATIVES AS HYPOGLYCEMIC AGENTS

[75] Inventors: David A. Clark, East Lyme, Conn.; Michael R. Johnson, Chapel Hill, N.C.

[73] Assignee: Pfizer Inc., New York, N.Y.

[21] Appl. No.: 460,848

[22] PCT Filed: Jun. 10, 1987

[86] PCT No.: PCT/US87/01356

§ 371 Date: Nov. 15, 1989

§ 102(e) Date: Nov. 15, 1989

[87] PCT Pub. No.: WO88/09661

PCT Pub. Date: Dec. 15, 1988

[51] Int. Cl.⁵ .................... C07D 263/08; A61K 31/42
[52] U.S. Cl. .................... 514/340; 514/342; 514/369; 514/376; 548/183; 548/229; 546/275; 546/280
[58] Field of Search ............... 514/340, 342, 369, 376; 546/275, 280; 548/183, 229

[56] References Cited

U.S. PATENT DOCUMENTS

| | | | |
|---|---|---|---|
| 2,909,467 | 10/1959 | Shapiro et al. | 548/227 |
| 4,340,605 | 7/1982 | Kawamatsu et al. | 546/280 |
| 4,407,811 | 10/1983 | Schnur | 548/226 |
| 4,430,337 | 2/1984 | Holland | 548/226 |
| 4,596,816 | 6/1986 | Meguro et al. | 514/374 |
| 4,617,312 | 10/1986 | Schnur | 514/369 |
| 4,687,777 | 8/1987 | Meguro et al. | 514/342 |
| 4,738,972 | 4/1988 | Eggler | 514/369 |
| 4,775,687 | 10/1988 | Meguro et al. | 514/369 |
| 4,791,125 | 12/1988 | Clark | 514/369 |
| 4,812,570 | 3/1989 | Meguro et al. | 546/280 |
| 4,873,255 | 10/1989 | Yoshioka et al. | 514/369 |
| 4,918,091 | 4/1990 | Cantello | 514/369 |

FOREIGN PATENT DOCUMENTS

| | | |
|---|---|---|
| 153682 | 1/1982 | German Democratic Rep. |
| 2080803 | 2/1982 | United Kingdom . |
| 2149405 | 6/1985 | United Kingdom . |
| 86/02073 | 4/1986 | World Int. Prop. O. |
| 86/02268 | 4/1986 | World Int. Prop. O. |

OTHER PUBLICATIONS

Chem. Abst. vol. 111, No. 7 Entry 57718e Abstracting EP294995.
Shapiro et al., J. Am. Chem. Soc., 81, 5646–5650 (1959).
Shapiro et al., J. Am. Chem. Soc., 81 6498–6504 (1959).
Kano et al., J. Org. Chem. 48, 3835–3837 (1983).
Kano et al., Heterocycles, 23, 395–398 (1985).

*Primary Examiner*—Donald G. Daus
*Attorney, Agent, or Firm*—Peter C. Richardson; J. Trevor Lumb; Robert K. Blackwood

[57] ABSTRACT

Certain 4-[2-(5-(optionally-substituted-aryl- and heteroaryl)oxazolidin-2-on-3-yl)alkyl]benzoic acids and ester, glycinamide, oxazole and thiazolidinedione derivatives thereof are useful as hypoglycemic agents.

22 Claims, No Drawings

OXAZOLIDIN-2-ONE DERIVATIVES AS HYPOGLYCEMIC AGENTS

BACKGROUND OF THE INVENTION

The present invention relates to hypoglycemic agents which are certain 4-[2-(5-aryl- and heteroaryloxazolidin-2-on-3-yl)alkyl]benzoic acids and ester, glycinamide, oxazole and thiazolidinedione derivatives thereof.

In spite of the early discovery of insulin and its subsequent wide-spread use in the treatment of diabetes, and the later discovery and use of sulfonylureas (e.g., chloropropamide, tolbutamide, acetohexamide, tolazamide) and biguanides (e.g., phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily, usually self, injection. Determination of the proper dosage of insulin requires frequent estimations of the sugar in the urine or in the blood. The administration of an excess dose of insulin causes hypoglycemia, with effects ranging from mild abnormalities in blood glucose to coma, or even death. Treatment of non-insulin dependent diabetes mellitus (Type II diabetes) usually consists of a combination of diet, exercise, oral agents, e.g., sulfonylureas, and in more severe cases, insulin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

In addition to the hypoglycemic agents cited above, a variety of other compounds have been reported to possess this type of activity, as reviewed by Blank [Burger's Medicinal Chemistry, Fourth Edition, Part II, John Wiley and Sons, N.Y. (1979), pp. 1057-1080].

Subsequently, Schnur, U.S. Pat. Nos. 4,332,952, 4,342,771, 4,367,234 and 4,617,312 disclosed various classes of 5-aryl- and 5-heteroaryl-substituted oxazolidine- and thiazolidine-2,4-diones; Kawamatsu et al., U.S. Pat. No. 4,461,902 described certain p-substituted-5-benzylthiazolidine-2,4-diones; and Holland, U.S. Pat. No. 4,430,337 described certain 5-alicyclic-substituted oxazolidine-2,4-diones; all as having hypoglycemic activity. More recently, Eggler et al. disclosed hypoglycemic thiazolidine-2,4-diones of the type

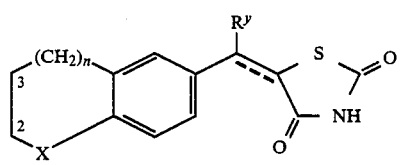

wherein the dotted line represents an optional double bond, n=0, 1 or 2; X is O, S, SO, $SO_2$, $CH_2$, CO, CHOH or $NR^x$; $R^x$ is an acyl group; $R^y$ is H, $CH_3$ or $C_2H_5$; variously and optionally substituted at the 2,3-positions of the X-containing heterocyclic ring.

A variety of compounds generally encompassed by the formula

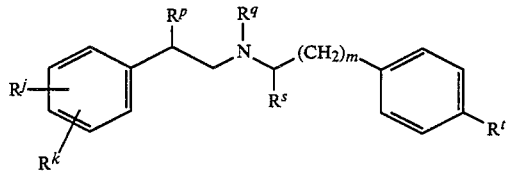

have also been recently disclosed as hypoglycemic and antiobesity agents, summarized as follows: Smith et al. U.S. Pat. No. 4,309,443 (including $R^j$=H, F, Cl, $CF_3$; $R^k$=H, F, Cl; $R^p$=OH; $R^q$=H; $R^s$=H, $CH_3$; m=1-5; $R^t$=CH=CH—COOH); Ainsworth et al. (I), U.S. Pat. No. 4,338,333 (including $R^j$, $R^k$, $R^p$, $R^q$ and $R^s$ the same as Smith et al.; m=1-6; $R^t$=O-$Z^a$—$CO_2H$; $Z^a$=alkylene, alkenylene or alkynylene of up to 10 carbons); Mills et al., U.S. Pat. No. 4,391,826 (including $R^j$=H or o-F; $R^k$=H; $R^p$=OH; $R^q$=H; $R^s$=H, $CH_3$ or $C_2H_5$; m=2; $R^t$=OH, alkanoyloxy, $CONH_2$, $CONHCH_3$, $COOCH_3$ or $COOC_2H_5$); Ainsworth et al. (II), U.S. Pat. No. 4,478,849 (including $R^j$, $R^k$, $R^p$, $R^q$, $R^s$ and m the same as Ainsworth et al. (I); $R^t$ is COOH or a salt, ester or amide thereof); Hindley, U.S. Pat. No. 4,593,023 (including $R^j$=H, halogen, $CF_3$; $R^k$=H or halogen; $R^p$ and $R^q$ are taken together with the carbon and nitrogen to which they are attached to form a 2-oxomorpholine ring; $R^s$=H or $CH_3$; m=1 or 2 and $R^t$=—O(CH$_2$)$_a$CO$_2$H or —COOH, or an ester thereof, where a=-1-6); Cantello, U.S. Pat. No. 4,607,033 (including $R^j$, $R^k$, $R^s$, $R^t$, and m the same as Hindley, but $R^p$ and $R^q$ taken together with the carbon and nitrogen to which they are attached to form a morpholine or homomorpholine ring; Ainsworth et al. (III), U.S. Pat. No. 4,596,800 ($R^j$, $R^k$, $R^p$, $R^t$, and m the same as Hindley, but $R^p$ and $R^q$ are taken together with the carbon and nitrogen to which they are attached to form a 2-hydroxymorpholine ring); Ainsworth et al. (IV), European Patent Application No. 40,915 (including $R^j$=m—$CH_3$; $R^k$=H; $R^p$=OH; $R^q$=H; m=1-3; $R^t$=—COOH); Borge et al., European Patent Application No. 142,102 (including $R^j$=H, halogen or $CF_3$; $R^k$=H or halogen; $R^p$=OH; $R^q$=alkyl; m=1 or 2; $R^t$=—O(CH$_2$)$_a$CO$_2$H or —COOH, or an ester thereof).

SUMMARY OF THE INVENTION

The present invention is directed to hypoglycemic 5RS racemic and 5R optically active oxazolidin-2-one compounds of the formula

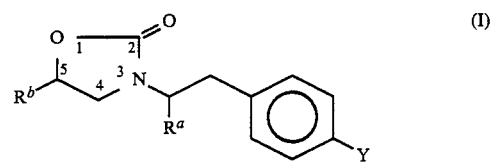

(I)

wherein $R^b$ is

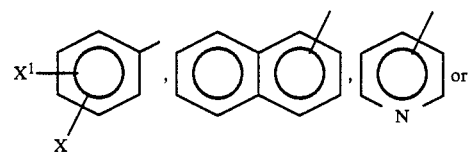

-continued

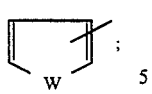

W is sulfur or oxygen;
X and X¹ are each independently H, Cl, F or CF₃;
Y is

—COOR¹, —CONCH₂CONR²R³,

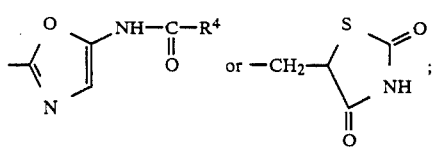

$R^a$, $R^1$, $R^2$ and $R^3$ are each independently H or CH₃; and $R^4$ is CH₃ or CF₃;

the pharmaceutically-acceptable acid addition salts thereof when Y is

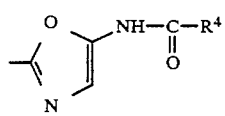

or $R^b$ is

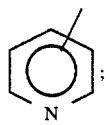

and the pharmaceutically-acceptable cationic salts thereof when Y is —COOH or

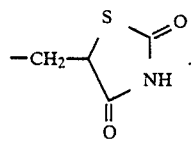

At least some, if not all of the present compounds of the formula (I) also show blood cholesterol lowering properties and so are valuable in reducing the incidence of cardiovascular disease. This property is a particularly valuable adjunct in the use of the present compounds in the treatment of diabetics, where cardiovascular disease is a leading cause of death.

The oxazolidin-2-one compounds of the formula (I) possess an asymmetric carbon at the 5-position of the ring which can exist in R- or S-configuration, for example:

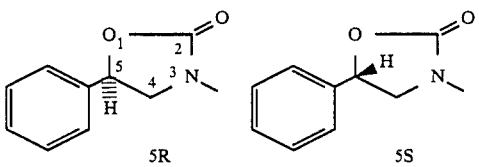

The expression "5RS racemic" refers to those compounds of the present invention which are unresolved, comprising equal parts of 5R and 5S isomers. The expression 5R optically active refers to those compounds of the present invention which have been resolved and have R stereo chemistry at ring position 5. The hypoglycemic activity of the present compounds resides primarily or completely in said 5R isomers.

The expression "pharmaceutically-acceptable cationic salts" is intended to define such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol), procaine, etc. An especially preferred such salt is the sodium salt.

The expression "pharmaceutically-acceptable acid addition salts" is intended to include such salts as the hydrochloride, hydrobromide, hydroiodide, nitrate, hydrogen sulfate, dihydrogen phosphate, mesylate, maleate, succinate, etc.

In compounds of the formula (I) as defined above, because of their ease of preparation and generally higher hypoglycemic activity, the preferred value of R is

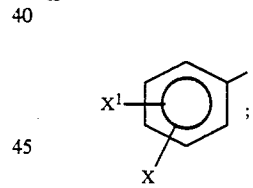

the preferred values of Y are —CONHCH₂CONH₂ and

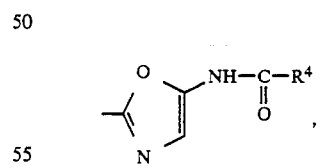

most particularly the latter, regardless of the value of $R^4$; the preferred value of $R^a$ is methyl; and the preferred values of X are m—Cl, p—Cl, m—F and m—CF₃, most particularly m—Cl, with X¹ as hydrogen; or X and X¹ as 3,4-dichloro.

Because they contain maximal hypoglycemic activity per unit weight, the optically active 5R compounds are preferred over the racemic 5RS compounds. When $R^a$ is methyl, a second asymmetric center is created at the carbon adjacent to the ring nitrogen, i.e., the 2-position of the side chain:

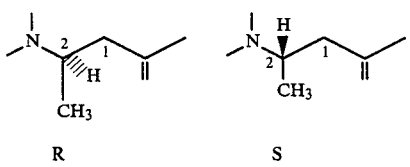

so-numbered when the compounds are named as 4-[2-(5-substituted-oxazolidin-2-on-3-yl)alkyl]benzoic acid derivatives. In this case, the 2R-(5R optically active variants are preferred over the corresponding diastereomeric 2S-(5R variants, while the 2R-(5R/2S-(5S [RR/SS] racemate is preferred over the 2R-(5S/2S-(5R [RS/SR] racemate.

Preferred species are readily defined by combining preferred values of X, $R^a$ and Y as detailed above.

The present invention is also directed to pharmaceutical compositions comprising a hypoglycemic effective amount of a compound of the formula (I) and a pharmaceutically-acceptable carrier; and to a method of treating hyperglycemia in a mammal which comprises treating said mammal with a hypoglycemic effective amount of said compound of the formula (I).

DETAILED DESCRIPTION OF THE INVENTION

The hypoglycemic acids (I, Y=COOH) of the present invention are readily and preferably prepared by reaction sequences which are summarized in Flowsheet 1. In that flowsheet, the compound of the formula (I) has been rewritten as

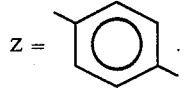

(I')

wherein $R^a$, $R^b$ and Y are as defined above; and $Z = $ ⌬

The intermediates (D), mixtures of diastereoisomers, are generically disclosed and in some cases specifically disclosed as hypoglycemic agents by Ainsworth et al. (II), and (IV), cited above, and are prepared substantially according to the alternative methods found in that reference. Referring to Flowsheet 1, the acid

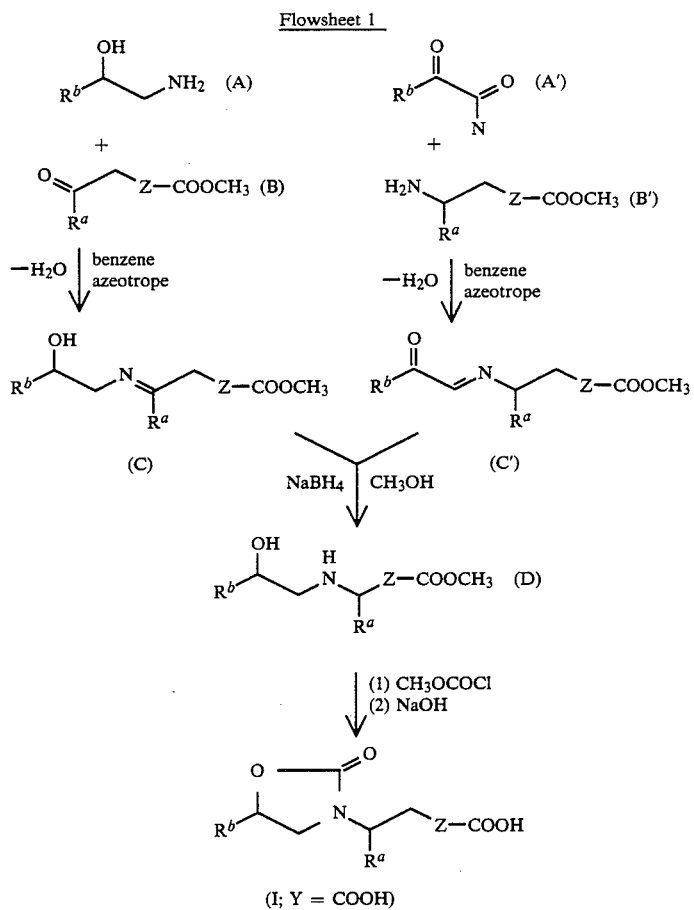

Referring to Flowsheet 1, the acid compounds (I, Y=COOH) are generally prepared from right and left hand portions (A)/(A') and (B)/(B'), one of which is an amine and the other a ketone or aldehyde, initially forming an imine (C)/(C'). The imine is readily formed by combining the amine and the carbonyl in an otherwise reaction-inert solvent which will azeotrope with water. Particularly useful solvents are benzene and toluene where water is readily removed by refluxing and collecting formed water in a Dean-Stark trap. Preferred is benzene, in which the reaction is readily accomplished at the reflux temperature of benzene at atmospheric pressure. The intermediate imine (C) is then reduced, conveniently with excess NaBH₄ in methanol, which is readily carried out under mild conditions, e.g., at 0°–50° C. It will be noted that the ketone carbonyl group of (C') is concurrently reduced to the carbinol group. When the starting materials (A) or (B') are racemic, and $R^a$ is methyl, the product (D) represents a pair of diastereomeric racemic compounds. Similarly, when $R^a$ is methyl and the optically active P-variant of the beta-hydroxy amine (A) is employed, the product will comprise two optically active diastereoisomers. In principle, whether racemic or optically active, these pairs of diastereomers can be separated at this stage by such methods as chromatography or fractional crystallization. For example, Ainsworth et al. (III), cited above, separated one of the diastereomeric racemic pair of the compound (D) wherein X=H and $R^a$=CH₃ (without assignment of stereochemistry). In present practice, it is preferred to defer such separation to the next stage, as discussed below.

Variations in this process will be evident to the practioner. For example, other ester radicals such as ethyl or benzyl can be substituted for the methyl group. Furthermore, a compound

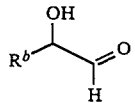 (A")

can be substituted for (A') in the right hand leg of Flowsheet 1, yielding

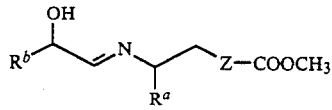 (C")

which is likewise reduced to the compound (D). In further variations, hydrogenation over a noble metal catalyst in a reaction-inert solvent is substituted for sodium borohydride in methanol; or the two stages are accomplished in a single stage under standard reductive amination (reductive alkylation) conditions. In either case, when hydrogen and noble metal catalyst are employed, care is taken to keep the conditions mild so as to avoid hydrogenolytic loss of the benzylic hydroxy group.

As used in the preceeding paragraphs and elsewhere herein, the expression "reaction-inert solvent" refers to a solvent which does not interact with starting materials, reagents, intermediates or products in a manner which adversely affects the yield of the desired product.

The intermediates of the formula (D) are then reacted with methyl chloroformate in a reaction-inert solvent such as CH₂Cl₂ in the presence of a tertiary amine at 0°–50° C., thus forming an intermediate carbamate of the formula

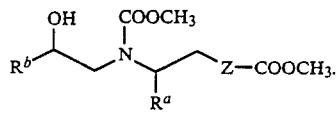

The latter, usually isolated only in crude form, is then reacted with excess of a strong base (e.g., NaOH) in an aqueous organic solvent, again at 0°–50° C., in order to simultaneously cyclize to the oxazolidinone and hydrolyze the methyl ester to form the carboxylic acid of the formula (I) wherein Y is COOH. The latter is generally isolated as the free acid by acidification of the reaction mixture and extraction into an organic solvent.

When $R^a$ is methyl (and separation has not been accomplished at an earlier stage), the initially formed product will be a mixture of 2 dl pairs or racemates (RR/SS) and RS/SR) when the starting amine is racemic, and two optically active diastereoisomers when the amine is optically active. In either case, we have found that these isomeric materials are readily separated by column chromatography. Generally, the more polar RR/SS racemate or 2S-(5R diastereoisomer is the more active as a hypoglycemic agent.

The starting materials required for the synthesis of the compounds of the formula (I) wherein Y is COOH are readily available commercially or according to literature methods. For example, racemic 2-amino-1-phenylethanol is commercially available or, along with its analogs, according to the methods of Collin et al., *J. Med. Chem.*, vol. 13, pp. 674–680 (1970) and Lednicer et al., loc. cit.; vol. 11, pp. 1258–1262 (1968). Optically active R-2-amino-1-aryl- or heteroarylethanol analogs are generally prepared by resolution of the corresponding racemate by forming diastereomeric salts with an optically active acid. For example, R-2-amino-1-phenylethanol is prepared according to Preparation 3 below. Phenylglyoxal is also commercially available or, like its analogs, according to the methods of Ainsworth et al. (II), cited above, and Reed, European Patent Application No. 201,221. Methyl 4-(2-oxopropyl)benzoate, as well as methyl 4-(2-aminoethyl)benzoate and methyl RS-, R- and S-4-(2-aminopropyl)benzoate are also available according to the methods of Ainsworth et al. (II), cited above.

The hypoglycemic acids of the formula (I) wherein Y is COOH also serve as intermediates for the further hypoglycemic compounds of the formula (I) wherein Y is other than —COOH, as illustrated in Flowsheet 2 (where compounds of the formula I have been further rewritten as $R^c$—Y). In general, the acid is first converted to the acid chloride (E) by conventional methods, e.g., reaction with excess thionyl chloride in a reaction-inert solvent at 30°–100° C. Well suited as solvent in the present case is benzene with the reaction carried out at the reflux temperature of the reaction mixture. Once the reaction is complete, the solvent and excess reagent are simply removed by stripping, ultimately under high vacuum.

Flowsheet 2

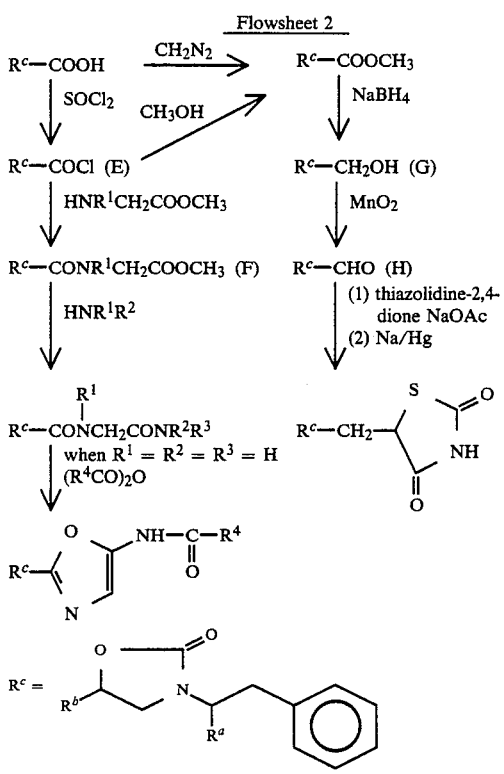

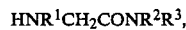

The glycinamides of the formula (I), wherein R is —CONR¹CH₂CONR²R³ can be prepared directly from the acid chloride by conventional reaction with glycinamide or an appropriate derivative, i.e.,

HNR¹CH₂CONR²R³, in a reaction-inert solvent such as $CH_2Cl_2$ in the presence of sufficient of a tertiary amine (such as triethylamine) to neutralize the co-produced HCl at 0°–50° C. The glycinamide is conventionally obtained from glycine methyl ester or sarcosine methyl ester.

Alternatively and preferably, said glycinamides of the formula (I) are obtained by initial reaction of glycine methyl ester or sarcosine methyl ester with the acid chloride (E) to form the methyl ester (F). The reaction is generally carried out in a reaction-inert solvent such as $CH_2Cl_2$ in the presence of a tertiary amine (such as triethylamine) in an amount at least sufficient to consume co-produced HCl. Temperature is not critical, 0°–50° C. being generally satisfactory. It is convenient to form the free base form of the glycine or sarcosine methyl ester in situ from the corresponding hydrochloride salt in the desired solvent and simply add the acid chloride and tertiary amine to the dried solution of glycine or sarcosine methyl ester.

The resulting methyl ester (F) is then reacted with the appropriate amine HNR²R³ [NH₃, NH₂CH₃ or NH(CH₃)₂] to form the desired glycinamide of the formula (I) wherein Y is —CONR¹CH₂CONR¹R², generally carried out by contacting the ester with an excess of the amine in a reaction-inert solvent at 0°–50° C., conveniently by saturating a methanol solution of the ester (F) with the gaseous amine at 0°–5° C. and allowing the reaction to proceed until complete at ambient temperature.

If the 2-(substituted)-5-(acylamino)oxazole, i.e., the compound of the formula (I) wherein Y is

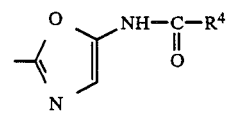

is desired, the glycinamide (I) wherein Y is —CONH—CH₂—CONH₂ is reacted with trifluoroacetic anhydride (when R⁴ is CF₃) or acetic anhydride, (when R⁴ is CH₃), in the presence of a strong acid catalyst, such as CF₃COOH, with or without the presence of a reaction-inert solvent such as $CH_2Cl_2$, at 20°–50° C. Generally, the more vigorous conditions (neat, at 50° C.) are employed when R⁴ is CH₃, while milder conditions (diluted in solvent, at ambient temperature) are employed when R⁴ is CF₃.

When the methyl ester of the formula (I) wherein $R^a$ is COOCH₃ is desired, the acid chloride (E) is conventionally reacted with excess methanol in the presence of a tertiary amine. Alternatively, the methyl ester is obtained directly from the acid by conventional reaction with diazomethane in a reaction-inert solvent such as ether/methanol. Those skilled in the art will recognize that other conventional methods can be used to convert the acid to the methyl ester, e.g., mixed anhydride procedures.

The methyl ester is also well suited as an intermediate in the preparation of the compounds of the formula (I) wherein Y is a (thiazolidine-2,4-dion-5-yl)methyl group,

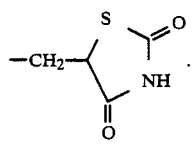

Thus, following the right hand of Flowsheet 2, conventional LiAlH₄ reduction of the methyl ester produces the hydroxymethyl compound (G) and conventional MnO₂ oxidation the aldehyde (H). Finally, the aldehyde (H) is conventionally condensed with thiazolidine-2,4-dione in the presence of a base such as sodium acetate in a reaction-inert solvent such as dimethylformamide at elevated temperature (125°–175° C.), producing the intermediate benzylidene:

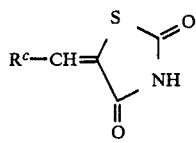

which is conventionally reduced, e.g., with excess sodium amalgam in a reaction-inert solvent such as methanol at 0°–50° C., conveniently at ambient temperature, with optional isolation of the product as a cationic salt.

The pharmaceutically acceptable cationic salts of the compounds of the present invention are more generally prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of a different salt of the cation (sodium ethylhexanoate, magnesium oleate), employing a solvent in which the desired cationic salt precipitates, or can be otherwise isolated by concentration and addition of a non-solvent.

The pharmaceutically acceptable addition salts are similarly formed by reacting the base form of the present compounds with the appropriate acid of addition, again usually one equivalent, in a co-solvent. Typical acids are HCl, HNO$_3$, H$_2$SO$_4$ (forming the sulfate with 0.5 molar equivalent, the hydrogen sulfate with 1 molar equivalent), CH$_3$SO$_3$H and p-CH$_3$C$_6$H$_4$SO$_3$H. The acid addition salts are isolated in the same manner as the cationic salts.

The compounds of the formula (I), as defined above, are readily adapted to clinical use as antidiabetic agents. The activity required for this clinical use is defined by the test for hypoglycemic effect in ob/ob mice by the following procedure:

Five to eight week old C57 BL/6J-ob/ob mice (obtained from Jackson Laboratory, Bar Harbor, Me.) were housed five per cage under standard animal care practices. After a one-week acclimation period, the animals were weighed and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days with drug (5-50 mg/kg), a positive control (50 mg/kg of ciglitazone; U.S. Pat. No. 4,461,902; Sohda et al., *Chem. Pharm. Bull.*, vol. 32, pp. 4460-4465, 1984), or vehicle. All drugs were administered in a vehicle consisting of 0.25% w/v methylcellulose. On day 5, the animals were weighed again and bled (via the ocular route) for blood metabolite levels. The freshly collected samples were centrifuged for two minutes at 10,000 xg at room temperature. The supernatant was analyzed for glucose, for example, by the ABA 200 Bichromatic Analyzer (a registered trademark of Abbott Laboratories, Diagnostics Division, 820 Mission Street, So. Pasadena, Calif. 91030), using the A-gent (also a registered trademark of said Abbott Laboratories) glucose UV reagent system (hexokinase method) using 20, 60 and 100 mg/dl standards, a modification of the method of Richterich and Dauwalder, Schweizerische Medizinische Wochenschrift, vol. 101, 860 (1971). Plasma glucose was then calculated by the equation, Plasma glucose (mg/dl) = Sample value × 5 × 1.67 = 8.35 × Sample value where 5 is the dilution factor and 1.67 is the plasma hematocrit adjustment (assuming the hematocrit is 40%).

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control (e.g., 130 mg/dl) is reported as 100%; a glucose half-way between that of the vehicle control and the positive control (e.g., 190 mg/dl) is reported as 50%; a glucose level which drops the glucose level 1.25 times that of the positive control (e.g., 100 mg/dl) is reported as 125%; and so forth.

The compounds of the formula (I), at a dose of 10 mg/kg, typically show from 21% to 127% glucose normalization, the more active compounds being in the range of 71% to 127%. For example, the optically active 2R-(5R compounds of the formula (I) wherein R$^b$ is m-chlorophenyl, R$^a$ is CH$_3$ and Y is

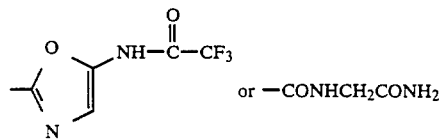

both show 100% glucose normalization at 10 mg/kg dose. Racemic RR/SS compounds of the formula (I) wherein R$^b$ is m-chlorophenyl, p-chlorophenyl or p-fluorophenyl, R$^a$ is CH$_3$ and Y is

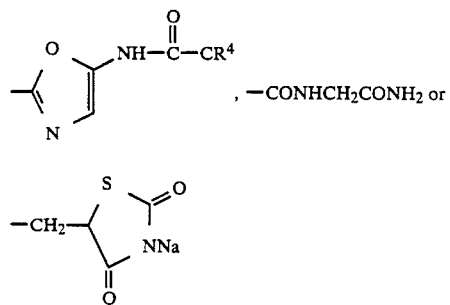

are generally in the more active range of 71%-127% at 10 mg/kg.

The conclusion that present compounds also possess valuable cholesterol lowering properties is based on the following study employing racemic RR/SS 2-[4-(2-(5-(3-chlorophenyl)oxazolidin-2-on-3-yl)propyl]phenyl]-5-(trifluoroacetylamino)oxazole, the product of Example 22 below. Mice (strain C57BR/cd J), obtained from Jackson Laboratories were used at age 6-12 weeks, following 2-4 weeks acclimation in our laboratories, having free access to water and standard laboratory chows. Animals were divided randomly into three groups of 6-8 animals. One group was maintained on the standard laboratory chow. The remaining two groups were placed on a diet containing 0.75% cholesterol, 31% sucrose, 15.5% starch, 20% casein, 17% cellulose, 4.5% corn oil, 5% coconut oil, 0.25% cholic acid, 4% salts and 2% vitamin mix for 18 days; and dosed daily at 9-11 a.m. for the final 5 days by oral gavage, the control group with 5 ml/Kg of vehicle (0.25% methyl cellulose) and the test group with drug (20 mg/Kg in vehicle). After the fourth day of dosing, the animals were fasted overnight, starting at 5 p.m. The following morning a fifth and final dose of the drug was administered to the test group and three hours later the animals sacrificed by decapitation. Blood from the body trunk was collected and allowed to clot, and the serum assayed enzymatically, using an Abbott VP automated analyzer, for HDL cholesterol, LDL and VLDL cholesterol, and total cholesterol, with the following results:

| | LDL/VLDL Cholesterol (mg/dl) | HDL Cholesterol (mg/dl) | Total Cholesterol (mg/dl) | LDL + VLDL/ HDL Ratio |
|---|---|---|---|---|
| Normal Diet | 100 | 50 | 150 | 2 |
| High Cholesterol Diet | 170 | 55 | 225 | 3.1 |
| High Cholesterol Diet + Drug | 60 | 45 | 105 | 1.3 |

Whether judged on the basis of LDL/VLDL cholesterol levels, total cholesterol levels or the ratio of LDL+VLDL/HDL, the tested drug shows a highly favorable result.

Whether used as hypoglycemics or in lowering blood cholesterol levels, or for both of these effects, the compounds of the formula (I) are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds are generally used in pharmaceutical preparations containing the compound, or pharmaceutically acceptable acid salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition slats of the compounds. The injectable solutions prepared in this manner can then be administered intravenously, intraperitoneally, subcutaneously, or intramuscularly, with intramuscular administration being preferred in man.

The present invention is illustrated by the following examples. However, it should be understood that the invention is not limited to the specific details of these examples.

EXAMPLE 1

Racemic 4-[2-(5-(3-Chlorophenyl)oxazolidin-2-on-3-yl)propyl]-benzoic Acids (Formula I, $R^a$=CH$_3$, $R^b$=m-ClC$_6$H$_4$, Y=COOH)

Step 1. 2-(3-Chlorophenyl)-2-hydroxyethylamine (24.4 g, 0.142 mol) and methyl 4-(2-oxopropyl)benzoate (26 g, 0.135 mol) were combined and refluxed in 500 ml toluene for 3 hours, collecting formed H$_2$O with a Dean-Stark trap. The reaction mixture was cooled and stripped of solvent to yield intermediate methyl 4-[2-(2-(3-chlorophenyl)-2-hydroxyethylimino)propyl]benzoate.

Step 2. The entire batch of imine of the preceding step was taken up in cold CH$_3$OH at 0° C. With stirring and maintaining temperature less than 10° C., NaBH$_4$ (48 g) was added portionwise over 1 hour. The mixture was then stirred for 18 hours at room temperature, concentrated to low volume in vacuo, diluted with 1000 ml H$_2$O and extracted 3×750 ml CHCl$_3$. The organic layers were combined, washed with saturated NaCl, dried (MgSO$_4$), stripped, the residue taken up in minimal 2.5% CH$_3$OH/CH$_2$Cl$_2$, filtered through silica gel with 10% CH$_3$OH/CH$_2$Cl$_2$ as eluant and stripped to yield methyl 4-[2-(2-(3-chlorophenyl)-2-hydroxyethylamino)propyl]benzoate, 36.0 g, as an oil.

Step 3. The product of preceding Step 2 (36 g, 0.103 mol) was dissolved in 500 ml CH$_2$Cl$_2$, stirred and cooled to 0° C. Triethylamine (16.8 ml, 0.120 mol) was added, followed by methyl chloroformate (9.3 ml, 0.120 mol) added over 5 minutes. The mixture was warmed and stirred at room temperature for 2 hours. More triethylamine (3 ml) and methyl chloroformate (2 ml) were added and the mixture stirred for 2 more hours, then stripped of solvent and the residual gum taken up in 500 ml CH$_3$OH and 500 ml tetrahydrofuran and cooled to 0° C. NaOH (1N, 500 ml) was added and the mixture stirred 16 hours at ambient temperature, then concentrated to 750 ml in vacuo, acidified with cold 10% HCl, and extracted 3×750 ml ethyl acetate. The combined organic layers were washed with saturated NaCl, dried (MgSO$_4$), stripped and chromatographed on silica gel using 1:1 ethyl acetate: hexane/5% CH$_3$CO$_2$H as eluant. The first product to elute was the less polar, title RS/SR diastereomeric dl pair, 15.0 g, which is less effective in lowering blood glucose. Later eluting more polar fractions were combined and stripped to yield the more active RR/SS diastereomeric dl pair, 13.3 g; m.p. 157°-158° C.

Analysis calculated for C$_{19}$H$_{18}$O$_4$NCl: C, 63.42; H, 5.05; N, 3.89%. Found: C, 63.26; H, 4.98; N, 3.79%.

EXAMPLES 2-6

Additional Racemic Compounds of the Formula (I) Wherein $R^a$=CH$_3$ and Y=COOH

Using the appropriate 2-(substituted phenyl)-2-hydroxyethylamine and methyl 4-(2-oxopropyl)benzoate, the stepwise methods of Example 1 were employed to prepare the following additional compounds of the formula I wherein $R^a$=CH$_3$ and Y=COOH were prepared, each separated chromatographically into racemic RS/SR (less polar) and RR/SS (more polar) diastereomeric (+) pairs:

| Example No. | R$^b$ |
| --- | --- |
| 2 | 4-ClC$_6$H$_4$ |
| 3 | 2-ClC$_6$H$_4$ |
| 4 | 3-CF$_3$C$_6$H$_4$ |
| 5 | C$_6$H$_5$ |
| 6 | 3-FC$_6$H$_4$ |

The appropriate 2-(2,5-dichloro)phenyl, 3,5-di(trifluoromethyl)phenyl, 2-chloro-3-fluorophenyl, 2-(trifluoromethyl)-4-chlorophenyl, 1-naphthyl, 2-naphthyl, 2-pyridyl, 3-pyridyl, 4-pyridyl, 2-furyl, 3-furyl, 2-thienyl, or 3-(thienyl)-2-hydroxyethylamine is substituted for the 2-(3-chlorophenyl)-2-hydroxyethylamine in Example 1 permits preparation of the corresponding compounds wherein R$^a$=CH$_3$, Y=COOH and R$^b$ is 2,5-dichlorophenyl, 3,5-di(trifluoromethyl)phenyl, 2-chloro-3-fluorophenyl, 2(trifluoromethyl)-4-chlorophenyl, 1-naphthyl, 2-naphthyl, 2-pyridyl, 3-pyridyl, 4-pyridyl, 2-furyl, 3-furyl, 2-thienyl or 3-thienyl.

EXAMPLE 7

Racemic 4-[2-(5-[3-(trifluoromethyl)phenyl]oxazolidin-2-on-3-yl)ethyl]benzoic Acid m-(Trifluoromethyl)phenylglyoxal (2.5 g) and methyl p-(2-aminoethyl)benzoate (1.85 g) were refluxed in benzene for 3 hours with azeotropic removal of water, then stripped to yield the imine. The latter was taken up in 100 ml CH$_3$OH, NaBH$_4$ (2.5 g) was added over 0.5 hours and the mixture stirred for 12 hours. H$_2$O (100 ml) was added and the mixture extracted 2×150 ml CHCl$_3$. The organic layers were combined, washed with saturated NaCl, dried (MgSO$_4$), stripped and the residue filtered through a short silica gel column using 19:1 CH$_3$OH:CHCl$_3$ as eluant. Fractions 4 and 5 of five fractions were combined and stripped to yield purified methyl 4-[2-(3-(trifluoromethyl)phenyl)-2-hydroxyethylamino]benzoate. The latter was then converted to present title product by the method of Step 3 of Example 1.

EXAMPLE 8

Optically Active 4-[2R- and 2S-(5R-(3-Chlorophenyl)oxazolidin-2-on-3-yl)propyl]-benzoic Acids Subjecting R-2-(3-chlorophenyl)-2-hydroxyethyl amine and racemic methyl 4-(2-oxopropyl)benzoate to the stepwise methods of Example 1 produced less polar 2S(5R- and more polar 2R(5R- title products.

EXAMPLE 9

Racemic RR/SS Methyl 4-[2-(5-(3-Chlorophenyl)oxazolidin-2-on-3-yl)propyl]-benzoate Excess diazomethane in ether was prepared by standard methods from N-methyl-N'-nitro-N-nitrosoguanidine, 40% KOH and ether. More polar (RR/SS) title product of Example 1 (50 mg) was suspended in 10 ml ether and dissolved by adding 2 ml CH$_3$OH. The solution was cooled to 0° C. and the excess CH$_2$N$_2$ in ether added. After stirring at 0° C. for 20 minutes and room temperature for 2 hours, the mixture was stripped to a semisolid residue which was taken up in minimal CH$_2$Cl$_2$ and chromatographed on 10 g silica gel with 1:49 CH$_3$OH:CH$_2$Cl$_2$ as eluant, collecting 5 ml fractions. Fractions 60–74 were combined, stripped to a gum and the gum crystallized by trituration with ether to yield title product; 20 mg; m.p. 120°–121° C.

In like manner, the other carboxylic acid products of Examples 2–8 are converted to the corresponding methyl esters.

EXAMPLE 10

Racemic RR/SS N$^2$-[4-[2-(5-(3-chlorophenyl)oxazolidin-2-on-3-yl)propyl]benzoyl]glycinamide (Formula I, R$^a$=CH$_3$, R$^b$=m-ClC$_6$H$_4$, Y=CONHCH$_2$CONH$_2$)

Step 1. The RR/SS more polar title product of Example 1 (13.3 g, 0.037 mol) and 50 ml SOCl$_2$ were heated at reflux in 500 ml C$_6$H$_6$ for 3 hours, then stripped, chased with fresh benzene and pumped to dryness for 1 hour under high vacuum to produce substantially solvent and reagent free acid chloride.

Meanwhile, glycine methyl ester hydrochloride (12.5 g, 0.10 mol) was distributed between 200 ml CH$_2$Cl$_2$ and 10 ml H$_2$O. Ba(OH)$_2$.8H$_2$O (20 g) was added and the mixture swirled for 10 minutes. The organic layer was decanted and the aqueous layer extracted 1×200 ml fresh CH$_2$Cl$_2$. The CH$_2$Cl$_2$ layers were combined, dried (Na$_2$SO$_4$), filtered and cooled to 0° C.

Triethylamine (5 ml) and then the above acid chloride, dissolved in 200 ml CH$_2$Cl$_2$ was added to the glycine methyl ester solution. The reaction mixture was allowed to warm to ambient temperature and stirred for 8 hours at room temperature, washed in sequence with 100 ml each of 10% HCl, H$_2$O, 10% NaHCO$_3$ and saturated NaCl, dried (MgSO$_4$) and stripped to yield title product as an oil, all of which was used in the next step.

Step 2. The entire product of preceding Step 1 was dissolved in 500 ml CH$_3$OH, cooled to 0° C. and the solution saturated with NH$_3$ gas. The solution was warmed to room temperature, stirred 48 hours, stripped of excess NH$_3$ and solvent, the residue taken up in 500 ml ethyl acetate, washed with H$_2$O and saturated NaCl, and restripped to a foam. The foam was dissolved in a mixture of 25 ml methanol, 100 ml ethyl acetate, 100 ml CH$_2$Cl$_2$ and 200 ml ether heated on a steam bath, and slowly cooled to yield crystalline title product, 8.1 g; m.p. 158°–159° C.

Analysis calculated for C$_{21}$H$_{22}$O$_4$N$_3$Cl: C, 60.65; H, 5.33; N, 10.11%. Found: C, 60.28; H, 5.29; N, 9.90%.

A second crop, 6.5 g as a foam suitable for recrystallization or further chemical transformation below, was obtained by stripping the crystal mother liquor to dryness.

EXAMPLES 11–15

Additional Racemic RR/SS Compounds of the Formula (I) Wherein R$^a$=CH$_3$ and Y=CONHCH$_2$CONH$_2$ According to the stepwise procedure of Example 10, the more polar diastereomeric compounds of Examples 2–6 were converted to the following RR/SS diastereomeric compounds:

| Ex. No. | R$^b$ | m.p. (°C.) | High Resolution Mass Spectra |
| --- | --- | --- | --- |
| 11 | 4-ClC$_6$H$_4$ | 136–138 | — |
| 12 | 2-ClC$_6$H$_4$ | 75–87 | Calcd. 416.1213 |

-continued

| Ex. No. | $R^b$ | m.p. (°C.) | High Resolution Mass Spectra |
|---|---|---|---|
| 13 | 3-CF$_3$C$_6$H$_4$ | 60–64 | Found 416.1195 |
| 14 | C$_6$H$_5$ | — | — |
| 15 | 3-FC$_6$H$_4$ | 168–170 | — |

The corresponding compounds wherein $R^b$ is 2,5-dichlorophenyl, 3,5-di(trifluoromethyl)phenyl, 2-chloro-3-fluorophenyl, 2-(trifluoromethyl)-4-chlorophenyl, 1-naphthyl, 2-naphthyl, 2-pyridyl, 3-pyridyl, 4-pyridyl, 2-furyl, 3-furyl, 2-thienyl or 3-thienyl are prepared in like manner.

EXAMPLE 16

Racemic RS/SR
N$^2$-[4-[2-(5-(3-(trifluoromethyl)phenyl)oxazolidin-2-on-3-yl)propyl]benzoyl]glycinamide By the stepwise procedures of Example 10, the less polar RS/SR product of Example 4 was converted to present title product.

EXAMPLE 17

Optically Active
N$^2$-[4-[2R-(5R-(3-chlorophenyl)oxazolidin-2-on-3-yl)propyl]benzoyl]glycinamide By the stepwise procedure of Example 10, the more polar 2R-(5R- product of Example 8 was separately converted to present title product; m.p. 156°–158° C.

EXAMPLE 18

Optically Active
N$^2$-[4-[2S-(5R-(3-chlorophenyl)oxazolidin-2-on-3-yl)propyl]benzoyl]glycinamide By the stepwise procedure of Example 10, the less polar 2S-(5R- product of Example 8 was converted to present title product; m.p. 115°–125° C. (dec.).

Analysis calculated for C$_{21}$H$_{22}$O$_4$N$_3$Cl: C, 60.65; H, 5.34; N, 10.11%. Found: C, 60.24; H, 5.50; N, 9.82%.

EXAMPLE 19

Racemic RR/SS
N$^2$-Methyl-N$^2$-[4-[2-(5-(3-chlorophenyl)oxazolidin-2-on-3-yl)propyl]benzoyl]glycinamide (Formula (I), $R^a$=CH$_3$, $R^b$=m-ClC$_6$H$_4$, Y=-CON(CH$_3$)CH$_2$CONH$_2$)

Title product was prepared by substituting equivalent sarcosine methyl ester hydrochloride for glycine methyl ester hydrochloride in Step 1 of Example 10. After stripping away the methanolic NH$_3$ in Step 2, crude title product was purified by chromatography on silica gel using 1:19 CH$_3$OH:CH$_2$Cl$_2$ as eluant, m.p. 67°–70° C.

EXAMPLE 20

Racemic RR/SS
N$^1$-Methyl-N$^2$-[4-[2-(5-(3-chlorophenyl)oxazolidin-2-on-3-yl)propyl]benzoyl]glycinamide (Formula (I), $R^a$=CH$_3$, $R^b$=m-ClC$_6$H$_4$, Y=-CONHCH$_2$CONH(CH$_3$))

Title product was prepared by substituting CH$_3$NH$_2$ for NH$_3$ in Step 2 of Example 10. After stripping away the excess methanolic CH$_3$NH$_2$, the residue was taken up in ethyl acetate, washed with 10% HCl and then saturated NaCl, dried (MgSO$_4$) and restripped to yield title product as a foam.

EXAMPLE 21

Racemic RR/SS N$^1$,
N$^1$-Dimethyl-N$^2$-[4-[2-(5-(3-chlorophenyl)oxazolidin-2-on-3-yl)propyl]benzoyl]glycinamide (Formula (I), $R^a$=CH$_3$, $R^b$=m-ClC$_6$H$_4$, Y=—CONHCH$_2$CON(CH$_3$)$_2$)

Title product was prepared by substituting (CH$_3$)$_2$NH for NH$_3$ in Step 2 of Example 10, with crude product purified according to Example 17.

Analysis calculated for C$_{23}$H$_{26}$O$_4$N$_3$Cl: C, 62.25; H, 5.86; N, 9.47%. Found: C, 61.62; H, 6.12; N, 9.27%.

EXAMPLE 22

Racemic RR/SS
2-[4-[2-(5-(3-Chlorophenyl)oxazolidin-2-on-3-yl)propyl]phenyl]-5-[trifluoroacetylamino]oxazole (Formula (I), $R^a$ = CH$_3$, $R^b$ = m-ClC$_6$H$_4$, Y =

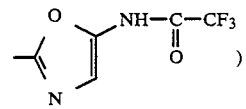
)

Title product of Example 10 (6.5 g) was dissolved in 200 ml of CH$_2$Cl$_2$ and cooled with stirring at 0° C. Trifluoroacetic anhydride (10 ml) was added over 2 minutes and the mixture stirred at ambient temperature for 1 hour, stripped of solvent, the residue taken up in 300 ml fresh CH$_2$Cl$_2$, washed with 10% NaHCO$_3$, saturated NaCl, dried (MgSO$_4$), restripped and the residue chromatographed on silica gel using 1:1 ethyl acetate:-hexane/5% acetic acid as eluant to yield title product, 6.2 g; m.p. 163°–164° C.

Analysis calculated for C$_{23}$H$_{17}$O$_4$N$_3$ClF$_3$: C, 55.93; H, 3.88; N, 8.53%. Found: C, 55.96; H, 3.82; N, 8.41%.

EXAMPLES 23–27

Additional Racemic RR/SS Compounds of the

Formula (I) Wherein $R^a$ = CH$_3$ and Y =

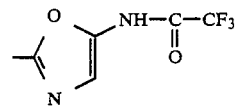

By the procedure of the preceding Example, the products of Examples 11–15 were converted to the following racemic RR/SS compounds of the Formula (I)

wherein $R^a$ = CH$_3$ and Y = 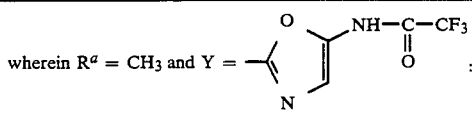 :

| Ex. No. | $R^b$ | m.p. (°C.) | Analysis |
|---|---|---|---|
| 23 | 4-ClC$_6$H$_4$ | 185–190 | — |
| 24 | 2-ClC$_6$H$_4$ | 105 | H.R.M.S. Calcd. 495.0987; Found 495.0924. |
| 25 | 3-CF$_3$C$_6$H$_4$ | 158–160 | Calcd. for C$_{24}$H$_{19}$O$_4$N$_3$F$_3$: C, 54.66; H, 3.63; N, 7.97%. |

-continued wherein $R^a = CH_3$ and $Y =$ 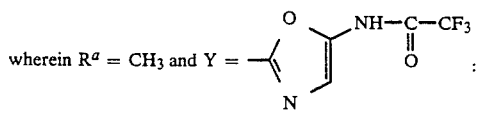

| Ex. No. | $R^b$ | m.p. (°C.) | Analysis |
|---------|-------|------------|----------|
|         |       |            | Found: C, 54.32; H, 3.60; N, 7.94%. |
| 26      | $C_6H_5$ | 80–85   | —        |
| 27      | 3-$FC_6H_4$ | 138–150 | —     |

The corresponding compounds wherein $R^b$ is 2,5-dichlorophenyl, 3,5-di(trifluoromethyl)phenyl, 2-chloro-3-fluorophenyl, 2-(trifluoromethyl)-4-chlorophenyl, 1-naphthyl, 2-naphthyl, 2-pyridyl, 3-pyridyl, 4-pyridyl, 2-furyl, 3-furyl, 2-thienyl or 3-thienyl are prepared in like manner.

EXAMPLE 28

Racemic RS/SR
2-[4-[2-(5-(3-Trifluoromethylphenyl)oxazolidin-2-on-3-yl)propyl]phenyl]-5-[(trifluoroacetyl)amino]oxazole By the method of Example 22, the product of Example 16 was converted to present title product, m.p. 60°–65° C.

EXAMPLE 29

Optically Active
2-[4-[2R-(5R-(3-Chlorophenyl)oxazolidin-2-on-3-yl)propyl]phenyl]-5-[(trifluoroacetyl)amino]oxazole By the method of Example 22, the title product of Example 17 was converted to present title product; m.p. 159°–160° C.

Analysis calculated for $C_{23}H_{19}O_4N_3ClF_3$: C, 55.93; H, 3.89; N, 8.51%. Found: C, 55.81; H, 4.20; N, 8.35%.

EXAMPLE 30

Optically Active
2-[4-[2S-(5R-(3-Chlorophenyl)oxazolidin-2-on-3-yl)propyl]phenyl]-5-[(trifluoroacetyl)amino]oxazole By the method of Example 22, the title product of Example 18 was converted to present title product; m.p. 80°–90° C.

Analysis calculated for $C_{23}H_{19}O_4N_3ClF_3$: C, 55.93; H, 3.89; N, 8.51%. Found: C, 55.56; H, 4.12; N, 8.09%.

EXAMPLE 31

Racemic RR/SS
2-[4-[2-(5-(3-Chlorophenyl)oxazolidin-2-on-3-yl)propyl]phenyl]-5-[acetylamino]oxazole (Formula (I), $R^a = CH_3$, $R^b = \underline{m}$-$ClC_6H_4$, $Y =$

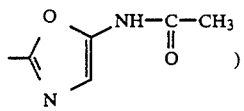
)

The title product of Example 10 (100 mg, 0.24 mmol) was suspended in 5 ml $CH_2Cl_2$. Trifluoroacetic acid (1 ml) and then acetic anhydride (5 ml) were added and the mixture stirred under $N_2$ for 16 hours. Additional acetic anhydride was added and the mixture warmed to 50° C. for 2 hours, then diluted with 25 ml $CH_2Cl_2$, washed in sequence with 25 ml $H_2O$, 25 ml saturated $NaHCO_3$, 25 ml $H_2O$ and 25 ml saturated NaCl, dried ($MgSO_4$), stripped and the residual tan gum chromatographed on silica gel with 1:19 $CH_3OH:CH_2Cl_2$ as eluant and monitoring by tlc (1:9 $CH_3OH:CH_2Cl_2$ as eluant). More polar fractions (Rf 0.3) were combined and stripped to yield title product, 30 mg; m.p. 78°–88° C. MS 439 (parent), 275, 260, 198, 184, 152, 137, 90, 65 and 42.

EXAMPLE 32

Optically Active
2-[4-[2R-(5R-(3-Chlorophenyl)oxazolidin-2-on-3-yl)propyl]phenyl]-5-[acetylamino]oxazole By the method of the preceding Example, the title product of Example 17 was converted to present title product; m.p. 88°–90° C.

EXAMPLE 33

Racemic RR/SS
4-[2-(5-(3-Chlorophenyl)oxazolidin-2-on-3-yl)propyl]-benzyl Alcohol Title product of Example 9 (1.0 g) in 30 ml ether and 20 ml tetrahydrofuran stirred at 0° C. was reacted with 200 mg of lithium aluminum hydride for 0.5 hours at 0° C. and 2 hours at room temperature. The reaction mixture was quenched by adding in sequence 0.2 ml $H_2O$, 0.2 ml 15% NaOH and 0.6 ml $H_2O$. After stirring 0.5 hour, the reaction mixture was filtered and the solids washed with ether. The combined filtrate and wash was washed with saturated NaCl, dried ($MgSO_4$), flash chromatographed on silica gel using 1:1 ether:hexane/2.5% acetic acid as eluant, and the eluate stripped to yield title product as an oil, 200 mg; tlc Rf 0.35 (same eluant).

EXAMPLE 34

Racemic RR/SS
4-[2-(5-(3-Chlorophenyl)oxazolidin-2-on-3-yl)propyl]-benzaldehyde

The product of the preceding Example (200 mg) and 750 mg $MnO_2$ were refluxed in 25 ml benzene for 2 hours using a Dean-Stark trap to remove formed $H_2O$. The reaction mixture was cooled, filtered over diatomaceous earth with ethyl acetate wash, and the combined filtrate and wash stripped to yield title product as an oil, 190 mg; tlc Rf 0.45 (1:1 ethyl acetate:hexane/2.5% acetic acid).

EXAMPLE 35

Racemic RR/SS Sodium Salt of
5-[4-[2-(5-(3-Chlorophenyl)oxazolidin-2-on-3-yl)propyl]benzyl]thiazolidine-2,4-dione (Formula (I), $R^a = CH_3$, $R^b = \underline{m}$-$ClC_6H_4$, $Y =$

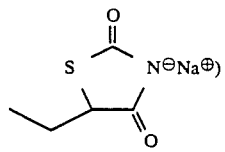)

Step 1. The product of the preceding Example (190 mg, 0.56 mmol) was condensed with thiazolidine-2,4-dione (66 mg, 0.56 mmol) in 1 ml dimethylformamide in the presence of sodium acetate (115 mg, 1.4 mmol) at 150° C. for 1 hour. The reaction mixture was removed from the heating bath and stripped under high vacuum to yield intermediate 5-[4-[2-(5-(3-chlorophenyl)ox-azolidin-2-on-3-yl)propyl]benzylidene]thiazolidine-2,4-dione.

Step 2. The entire product of preceding Step 1 was dissolved in 20 ml CH3OH. Excess Na/Hg amalgam was added and the mixture stirred for 48 hours. The solution was decanted, stripped, taken up in ethyl acetate, washed with saturated NaCl, dried (MgSO4), concentrated to 1 ml, diluted with excess sodium ethyl hexanoate in ethyl acetate, stirred for 6 hours and title product recovered by filtration; m.p. 110°–120° C.

Additional compounds wherein $R^b$ has other values as exemplified above were prepared in like manner.

EXAMPLE 36

Racemic RR/SS
4-[2-(5-(3,4-Dichlorophenyl)oxazolidin-2-on-3-yl)propyl]benzoic Acid (Formula (I), $R^a$=CH3, $R^b$=3,4-Cl2C6H3, Y=-COOH)

By the stepwise procedure of Example 1, substituting a molar equivalent of 2-(3,4-dichlorophenyl)-2-hydroxyethylamine for 3-chloro analog, title product was prepared in similar yield; m.p. 197°–198° C.

EXAMPLE 37

Racemic RR/SS
$N^2$-[4-[2-(5-(3,4-dichlorophenyl)oxazolidin-2-on-3-yl)propyl]benzoyl]glycinamide (Formula (I), $R^a$=CH3, $R^b$=3,4-Cl2C6H3, Y=—CONHCH2CONH2)

By the stepwise procedures of Example 10, the product of the preceding Example was converted to present title product; m.p. 90°–100° C.

EXAMPLE 38

Racemic RR/SS
2-[4-[2-(3,4-Dichlorophenyl)oxazolidin-2-on-3-yl)propyl]phenyl-5-[trifluoroacetylamino]oxazole (Formula (I), $R^a$ = CH3, $R^b$ = 3,4-Cl2C6H3,

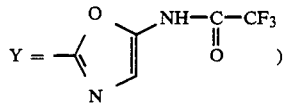
)

By the method of Example 22, the product of the preceding Example was converted to present title product; m.p. 134°–135° C.

PREPARATION 1 m-(Trifluoromethyl)phenacyl Bromide m-(Trifluoromethyl)acetophenone (10 g, 0.054 mol) was dissolved in 100 ml acetic acid. Bromine (9.1 g, 0.057 mol) was separately dissolved in 20 ml acetic acid and added portionwise over 0.5 hours to the acetophenone solution. The mixture was stirred for 15 hours, poured onto 150 g ice and extracted with 300 ml ether. The organic layer was washed 1×300 ml H2O, 1×300 ml saturated NaCl, dried (MgSO4) and evaporated to yield title product as a pale yellow liquid.

PREPARATION 2 m-(Trifluoromethyl)phenylglyoxal

The product of the preceding Preparation (10 g) was dissolved in 50 ml dimethylsulfoxide and allowed to stand for 24 hours, then poured over 100 g ice and extracted with 150 ml ether. The ether layer was washed with saturated NaCl, dried and stripped to yield title product as an oil, used directly in Example 7, above.

PREPARATION 3

(R)-2-(3-Chlorophenyl)-2-hydroxyethylamine

N-(t-Butoxycarbonyl)-D-alanine (5.0 g, 0.03 mol) was dissolved in 25 ml hot ethyl acetate. dl-3-(Chlorophenyl)-2-hydroxyethylamine (2.8 g, 0.015 mol) was separately dissolved in 5 ml ethyl acetate and added to the hot alanine solution. After heating the mixture for 2 minutes at reflux, the mixture was allowed to slowly cool to room temperature and stand for 1.5 hours, as product crystallized. The desired N-(t-Boc)-D-alanine salt of title product was recovered by filtration, washed with cold ethyl acetate and then ether, and air dried, 2.8 g; m.p. 115°–118° C.

$[alpha]_D^{24}$ = −29.89° (c=1.06 CH3OH). Recrystallization from 100 ml boiling ethyl acetate gave purified salt, 2.28 g; m.p. 114°–116° C.

$[alpha]_D^{24}$ = −30.86° (c=1 CH3OH).

The purified salt was distributed between 20 ml CHCl3 and 20 ml 2N NaOH. The organic layer was separated, washed with 20 ml H2O, then 20 ml saturated NaCl, dried (MgSO4) and stripped to yield title product as a colorless gum, 0.70 g.

$[alpha]_D^{24}$ = −41.04° (c=1.04 CH3OH).

We claim:
1. A 5-RS racemic or 5-R optically active oxazolidin-2-one compound of the formula

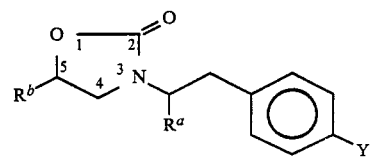

wherein
$R^b$ is

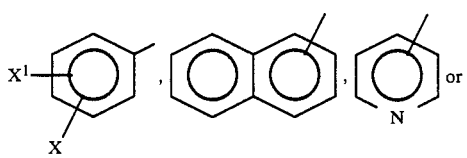

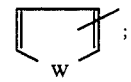

W is sulfur or oxygen;
X and $X^1$ are each independently H, Cl, F or CF3;
Y is

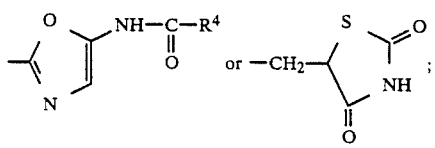

$R^a$, $R^1$, $R^2$ and $R^3$ are each independently H or $CH_3$; and $R^4$ is $CH_3$ or $CF_3$;

a pharmaceutically-acceptable acid addition salt thereof when Y is

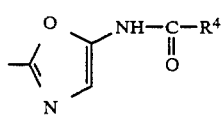

or $R^b$ is

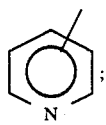

or a pharmaceutically-acceptable cationic salt thereof when Y is —COOH or

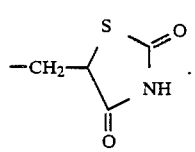

2. A compound of claim 1 wherein Y is —CONHCH$_2$CONH$_2$ or

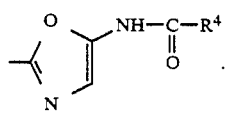

3. A compound of claim 1 wherein $R^a$ is $CH_3$ and $R^b$ is

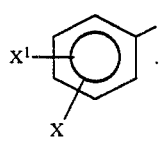

4. A compound of claim 2 wherein $R^a$ is $CH_3$ and $R^b$ is

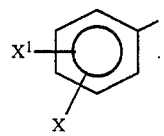

5. A compound of claim 1 which is optically active.

6. A compound of claim 4 which is optically active.

7. A compound of claim 1 wherein $R^b$ is m-chlorophenyl.

8. A compound of claim 4 wherein $R^b$ is m-chlorophenyl.

9. A compound of claim 6 wherein $R^b$ is m-chlorophenyl and the side chain carbon attached to the ring nitrogen is in the R-configuration.

10. The compound of claim 9 wherein Y is —CONHCH$_2$CONH$_2$.

11. The compound of claim 9 wherein Y is

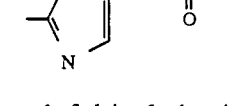

12. A compound of claim 6 wherein $R^b$ is m(trifluoromethyl)phenyl and the carbon attached to the ring nitrogen is in the R-configuration.

13. The compound of claim 12 wherein Y is —CONHCH$_2$CONH$_2$.

14. The compound of claim 12 wherein Y is

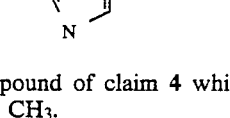

15. A compound of claim 4 which is racemic and wherein $R^a$ is $CH_3$.

16. A compound of claim 15 wherein Y is —CONHCH$_2$CONH$_2$ or

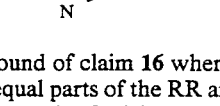

17. A compound of claim 16 wherein the racemate is comprised of equal parts of the RR and SS enantiomers.

18. A compound of claim 17 wherein $R^b$ is m-chlorophenyl, p-chlorophenyl, m-fluorophenyl, m-trifluoromethylphenyl or 3,4-dichlorophenyl.

19. The compound of claim 18 wherein $R^b$ is 3,4-dichlorophenyl and $R^4$ is $CF_3$.

20. The compound of claim 18 wherein $R^b$ is 3-chlorophenyl and $R^4$ is $CF_3$.

21. A pharmaceutical composition comprising a hypoglycemic effective amount of a compound of claim 1 and a pharmaceutically-acceptable carrier.

22. A method of treating hyperglycemia in a mammal which comprises treating said mammal with a hypoglycemic effective amount of a compound of claim 1.

* * * * *